United States Patent
Grynkiewicz et al.

(10) Patent No.: US 8,623,910 B2
(45) Date of Patent: *Jan. 7, 2014

(54) ISOFLAVONES FOR TREATING MUCOPOLYSACCHARIDOSES

(75) Inventors: Grzegorz Grynkiewicz, Lomianki (PL); Grzegorz Wegrzyn, Gdansk (PL); Barbara Szechner, Warsaw (PL); Wieslaw Szeja, Zernica (PL); Anna Tylki-Szymanska, Warsaw (PL); Alicja Wegrzyn, Gdansk (PL); Joanna Jakobkiewicz-Banecka, Gdansk (PL); Sylwia Baranska, Gdansk (PL); Barbara Czartoryska, Warsaw (PL); Ewa Piotrowska, Olsztyn (PL)

(73) Assignee: Instytut Farmaceutyczny, Warsaw (PL)

( * ) Notice: Subject to any disclaimer, the term of this patent is extended or adjusted under 35 U.S.C. 154(b) by 0 days.

This patent is subject to a terminal disclaimer.

(21) Appl. No.: 13/433,492

(22) Filed: Mar. 29, 2012

(65) Prior Publication Data

US 2012/0190642 A1 Jul. 26, 2012

Related U.S. Application Data

(63) Continuation of application No. 12/067,289, filed as application No. PCT/PL2006/000064 on Sep. 21, 2006, now Pat. No. 8,178,609.

(30) Foreign Application Priority Data

Sep. 21, 2005 (PL) .......................................... 377180

(51) Int. Cl.
    *A61K 47/32* (2006.01)
(52) U.S. Cl.
    USPC .......................................... 514/456; 549/403
(58) Field of Classification Search
    USPC .......................... 536/8; 549/403; 524/25, 456
    See application file for complete search history.

(56) References Cited

U.S. PATENT DOCUMENTS 6,399,107 B1    6/2002    Kessler et al.

FOREIGN PATENT DOCUMENTS

WO    00/37072 A1    6/2000

OTHER PUBLICATIONS

Piotrowska, E. et al., Genistein-mediated inhibition of glycosaminoglycan synthesis as a basis for gene expression-targeted isoflavone therapy for mucopolysaccharidoses, European Journal of Human Genetics, May 3, 2006, 846-852, 14, Nature Publishing Group, New York, NY, USA.
Wegrzyn, G. et al., A general model for genetic regulation of turnover of glycosaminoglycans suggests a possible procedure for prediction of severity and clinical progress of mucopolysaccharidoses, Medical Hypotheses, Jun. 31, 2004, 986-992, 62-6, Elsevier, Amsterdam, The Netherlands.
Mitropoulou, T. N. et al., In vitro Effects of Genistein on the Synthesis and Distribution of Glycosaminoglycans / Proteoglycans by Estrogen Receptor-positive and -negative Human Breast Cancer Epithelial Cells, Anticancer Research, May 31, 2002, 2841-2846, 22-5, The International Institute of Anticancer Research, Attiki, Greece.

*Primary Examiner* — Elli Peselev
(74) *Attorney, Agent, or Firm* — Matthias Scholl, PC; Matthias Scholl

(57) ABSTRACT

A method of treatment of mucopolysaccharidosis, the method including administering to a patient in the need of such treatment—a therapeutically effective amount of a natural isoflavone of formula (I), a derivative thereof, or a pharmaceutically acceptable salt thereof. A pharmaceutical composition including a pharmaceutically acceptable excipient; and a natural isoflavone of formula (I), a derivative thereof, or a pharmaceutically acceptable salt thereof, the natural isoflavone, the derivative thereof, or the pharmaceutically acceptable salt thereof being in a therapeutically effective amount for the treatment of mucopolysaccharidosis.

15 Claims, 2 Drawing Sheets

US 8,623,910 B2

ISOFLAVONES FOR TREATING MUCOPOLYSACCHARIDOSES

CROSS-REFERENCE TO RELATED APPLICATIONS

This application is a continuation of U.S. application Ser. No. 12/067,289 with a 371(c) date of Nov. 5, 2008, now issued as U.S. Pat. No. 8,178,609 on May 15, 2012, which is a National Stage Application under 35 U.S.C. §371 of Int'l Pat. Appl. No. PCT/PL2006/000064, filed on Sep. 21, 2006. Pursuant to 35 U.S.0 §119 and the Paris Convention Treaty, this application further claims the benefit of Polish Pat. Appl. No. 377180, filed on Sep. 21, 2005. The contents of all of the aforementioned applications, including any intervening amendments thereto, are incorporated herein by reference in their entirety.

CORRESPONDENCE ADDRESS

Inquiries from the public to applicants or assignees concerning this document should be directed to: MATTHIAS SCHOLL P.C., ATTN.: DR. MATTHIAS SCHOLL ESQ., 14781 MEMORIAL DRIVE, SUITE 1319, HOUSTON, TX 77079.

BACKGROUND OF THE INVENTION

1. Field of the Invention

The invention relates to the medical use of natural isoflavones and their semisynthetic derivatives for the therapeutic and/or prophylactic treatment of diseases, at the base of which lies an excessive production or storage of glycosaminoglycans, especially for the treatment of mucopolysaccharidoses.

2. Description of the Related Art

Natural isoflavones, present in most vascular plants, constitute a subclass of flavonoids characterized by the presence of two benzene rings linked to a group of three carbon atoms in their linear or ring form.

The main flavone ingredients of seeds *Glycine max* Merin (soya-bean) constitute β-D-glycosides, such as, genistin, daidzin and glycitin, while the corresponding to them aglycones (genistein, daidzein and glycitein) occur in up to one hundred times smaller quantities and appear in more considerable amounts only when being technologically processed, under heat treatment or due to fermentation.

Genistein (4',5,7-trihydroxy-3-phenylchromen-4-on) is a competitive inhibitor for protein tyrosine kinases (PTK), playing an important role as a structural analogue of adenosine triphosphate (ATP) (T. J. O'Dell et al., Nature, 353, p. 558 (1991). Research concerning the biological role of enzymes from the PTK group in the transmission of chemical signals cascade from the cell membrane receptors to the nuclear effectors modulating the gene expression and transcription, constitute one of the most promising trends in the medical chemistry (P. W. Groundwater et al., Progr. Med. Chem., 33, p. 233, 1996). At the same time it is expected that selective phosphorylation inhibitors will give rise not only to a new generation of drugs, for instance antineoplastic drugs, but also to compounds, which will inhibit the oncogenesis, thus preventing neoplastic diseases.

In medical respect, genistein is classified as phytoestrogen and is included among a new class of biological active compounds termed selective estrogen receptors modulators (SERM).

In Polish Pat. Appl. No. 346955 and in K. Polkowski et al. (Cancer Letters 203 (2004), 59-69) disclosed is the cytotoxic and cytostatic activity in vitro of several ethereal and ester derivatives of genistein, in which one hydrogen atom of at least one hydroxyl group at the positions 7 and/or 4' has been replaced by fatty acid radical, alkyloaryl, or saccharide groups.

In that application, as in the Polish Pat. Appl. No. 354794, disclosed is the manner for functionalizing the hydroxyl groups of genistein and a synthetic methodology applied to obtain new derivatives.

At the base of present invention lies the finding that genistein, like other isoflavones and semisynthetic derivatives thereof, causes a significant inhibition of glycosaminoglycans synthesis and in consequence of it would be useful for treatment of diseases caused by excessive production or storage of mucopolysaccharides.

The mucopolysaccharidoses (MPS) are the rare genetic conditions which inheritance is autosomal recessive (with exception of a mucopolysaccharidose of type II, MPS II, the inheritance of which is X-linked) (Kaye, Curr. Treat Opinions Neurol. 3 (2000), 249). The cause of each of the type of mucopolysaccharidose is a damage of a specific lysosomal enzyme taking part in the degradation of the mucopolysaccharides.

The mucopolysaccharides, at present called glycosaminoglycans (GAG), are chemical compounds produced by the most of tissues in mammals. They are, among other, responsible for the correct structure and functioning of connective tissue, for proper communication between the cells (including intracellular signaling owing to aided binding of signaling proteins with their receptors in the cell membranes) and for possibility of proper penetration of different substances into body tissues.

Most of the glycosaminoglycans occur in form of peptidoglycans, i.e., are connected by a covalent bond (usually by a residue of serine) with a proper peptide. In the regular cell occurs the permanent turnover of the glycosaminoglycans, it means synthesis of the new and degradation of the elder molecules. The breakdown of these compounds in the cells take place in the lysosomes by participation of a dozen or so enzymes specifically directed to these organelles (Kaplan et al., Proc. Natl. Acad. Sci. USA 74 (1977), 2026).

When one of the enzymes responsible for the breakdown of the mucopolysaccharides is deficient or its activity significantly decreased, the mucopolysaccharides will not be degraded and will accumulate in the lysosomes and in the intercellular space. The insufficiency of the lysosomal apparatus stimulates many compensatory processes, after depletion of which the complicated function and structure of the cell will be disturbed, leading to its destruction and, in consequence, giving rise to characteristic clinical symptoms.

In the pathomechanism of these diseases, the key significance has not only the mechanic results of the storage, but also the toxic and damaging effect of the accumulated compounds and cytokines.

Different types of mucopolysaccharidose disorders classified as Type I through IX and the deficient enzymes are listed in Table 1.

TABLE 1

Mucopolysaccharidoses classification*

| Type | Name of syndrome | Enzyme deficient |
|---|---|---|
| MPS I-H | Hurler syndrome | α-L-iduronidase |
| MPS I-S | Scheie syndrome | α-L-iduronidase |
| MPS I-H/S | Hurler-Scheie syndrome | α-L-iduronidase |
| MPS II | Hunter syndrome | iduronate sulphatase |
| MPS III A | Sanfilippo syndrome type A | heparan-N-sulphatase |
| MPS III B | Sanfilippo syndrome type B | N-acetyl-α-D-glucosaminidase |
| MPS III C | Sanfilippo syndrome type C | CoA-α-glucosaminide-N-acetyltransferase |

TABLE 1-continued

Mucopolysaccharidoses classification*

| Type | Name of syndrome | Enzyme deficient |
|---|---|---|
| MPS III D | Sanfilippo syndrome type D | N-acetyl-α-D-glucosaminide-6-sulfatase |
| MPS IV A | Morquio syndrome type A | N-acetyl-α-D-glucosaminide-6-sulfatase |
| MPS IV B | Morquio syndrome type B | B-galactosidase |
| MPS VI | Maroteaux-Lamy syndrome | N-acetylgalactosamine-4-sulfatase (acetylsulfatase) |
| MPS VII | Sly syndrome | B-glucuronidase |
| MPS IX | — | hyaluronidase |

*Neufeld, E. F. and Muenzer, J., The mucopolysaccharidoses. In: Scriver, C. R., Beaudet, A. L., Sly, W. S., Valle, D. (ed.): The metabolic and molecular bases of inherited diseases. New York: McGraw-Hill Co, 2001, 3421-3452; Węgrzyn G., Mukopolisacharydozy. Praktyka i Klinika Medyczna, 4/5 (2000), 5-18.

The accumulation of mucopolysaccharides in the lyzosomes causes gradual function impairment of cells, tissues and practically of all the organs. These diseases have a progressing character and an average time of a patient's survival amounts to a dozen or so years.

Until now in case of all mucopolysaccharidoses only symptomatic treatment was possible, it was not very efficient, although it could improve the comfort of life of the affected to a certain degree.

Some hopes were set on bone marrow transplantation, in order to introduce the cells producing the lacking enzymes to the organism of the sick person (Schiffmann and Brady, Drugs, 62 (2002), 733). However, this method proved not to be very efficient, and at the same time it is connected with a higher risk of complications.

Since recently, replacement therapy of mucopolysaccharidose of type I became possible, based on intravenous administration of the lacking recombinant enzyme—the α-L-iduronidase (Kakkis, Expert Opin. Investig. Drugs, 11 (2002), 675). Although clinical research has shown a very high efficacy of this type of treatment towards most of the organs, it must be say that because of the blood-brain barrier as a serious problem remain disturbances in functioning of the central nervous system, found in part of patients with MPS 1 (especially in type MPS 1-H).

Enzymatic replacement therapy in case of MPS 1 is actually the only one accessible method of causal treatment of mucopolysaccharidoses. Other MPS types are not treated at all or only symptomatic treatment could be applied, which proved to be not very effective. Consequently there is an urgent necessity to look for therapeutic methods for this group of chronic diseases, which in the absence of treatment lead to the premature death of patients.

The greatest problem with introducing enzymatic replacement therapy in other MPS types is the fact that in many types of this disease (MPS II, MPS IIIA, MPS IIIB, MPS IIIC, MPS IIID, MPS VII) severe neurological symptoms may occur related to the central nervous system, while in others types the largest changes are observed in the osteoarticular system (MPS IVA, MPS IVB, MPS VI). The penetration of the intravenously administered enzyme into the central nervous system is minimal, whereas the penetration into the bone is very impeded.

An approach to the treatment of mucopolysaccharidoses being alternative to the enzymatic replacement therapy can constitute the inhibition of the synthesis of the substrate, which cannot be degraded in the organisms of sick individuals (Wę egrzyn et al., Med. Hypothes., 62 (2004), 986).

The present invention is based on the unexpected finding that the natural isoflavone, genistein, added to the cultured fibroblasts derived from patients affected with MPS, in the concentration range of 10-30 micromoles/l, causes significant inhibition of glycosaminoglycans synthesis.

The incubations of cells derived from patients affected with different MPS types (MPS I, MPS II, MPS IIIA and MPS IIIB) with genistein has proved that in these cells the level of glycosaminoglycans not only did not increase but on the contrary significantly decreased, reaching after six days a level almost identical with the normal one. The results of these tests have been confirmed by electron microscope investigations of the cells, where the disappearance of deposits in fibroblasts cultured during one week in presence of genistein (in concentration of 10 micromolar units) has been observed. Similar effects were observed in consequence of fibroblasts incubation in presence of a soya-bean isoflavones extract, what indicates that these compounds and their derivatives could have similar activity as in the case of genistein.

The molecular mechanism of genistein activity as inhibitor of glycosaminoglycans synthesis has not been recognized, although it seems to be likely that it is related to the previous founding to inhibit tyrosine kinase activity of the epidermal growth factor receptor (EGFr) (Akiyama et al., J. Biol. Chem., 262 (1987), 5592). This factor is in turn essential for the effective glycosaminoglycans synthesis (Tirone et al., J. Biol. Chem., 272 (1997), 4787). Activation of EFGr can probably stimulate the system of intracellular signal transmission, leading to the effective expression of genes, which are coding the enzymes related to the process of glycosaminoglycans synthesis.

The fact that intravenously administered genistein crosses the blood-brain barrier in a rat with an effectiveness of about 10% opens further possibilities for treating some neurological symptoms in patients suffering from mucopolysaccharidoses, which at present is entirely impossible (Tai, J. Chromatogr. A 1073 (2005), 317).

BRIEF SUMMARY OF THE INVENTION

This invention is directed to the natural isoflavones and their semisynthetic derivatives which have been discovered to be useful in treatment of the diseases, at the base of which lies an excessive production or storage of glycosaminoglycans.

The invention provides a method for treating or preventing of a disease, at the base of which lies an excessive production or storage of glycosaminoglycans, the method comprising: administering to a patient in the need of such a treatment a therapeutically effective amount of natural isoflavones or their semisynthetic derivative or the pharmaceutically acceptable salts thereof.

The invention further provides a method for treating or preventing of a disease, at the base of which lies an excessive production or storage of glycosaminoglycans, the method comprising: administering to a patient in the need of such a treatment a pharmaceutical composition comprising pharmaceutically acceptable vehicles and/or excipients and a therapeutically effective amount of natural isoflavones or their semisynthetic derivative or the pharmaceutically acceptable salts thereof.

The invention further provides a method for treating or preventing of mucopolysaccharidose type I, the method comprising: administering to a patient in the need of such a treatment a therapeutically effective amount of natural isoflavones or their semisynthetic derivative or the pharmaceutically acceptable salts thereof.

The invention further provides a method for treating or preventing of mucopolysaccharidose type I, the method comprising: administering to a patient in the need of such a treatment a pharmaceutical composition comprising pharmaceutically acceptable vehicles and/or excipients and a therapeutically effective amount of natural isoflavones or their semisynthetic derivative or the pharmaceutically acceptable salts thereof.

BRIEF DESCRIPTION OF THE DRAWINGS

The invention is described hereinbelow with reference to accompanying drawings, in which.

DETAILED DESCRIPTION OF THE INVENTION

Figure 1:
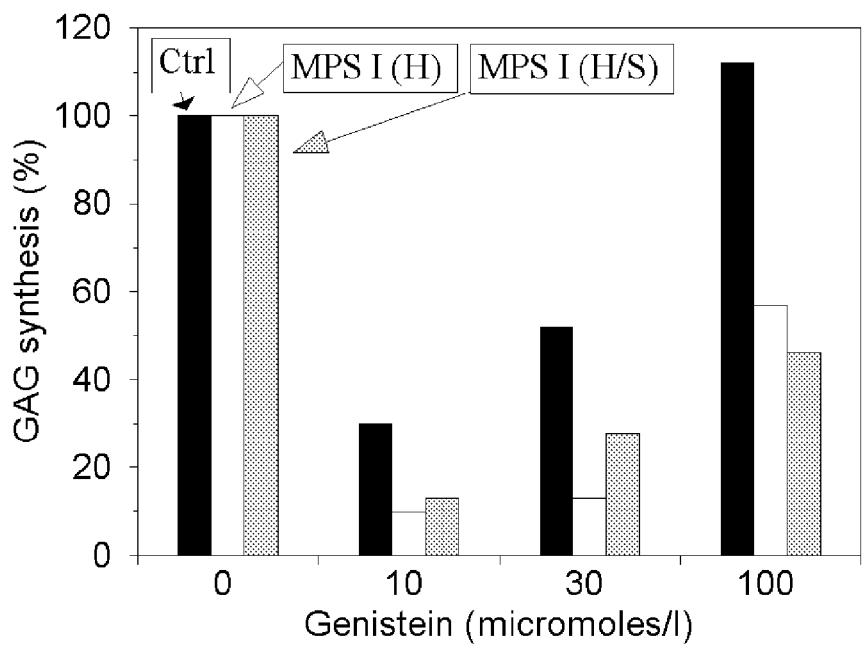
FIG. 1 shows glycosaminoglycans synthesis in fibroblasts of normal individuals (Ctrl) and of patients affected with MPS I, in vitro culture.

In view of their beneficial pharmacological properties, natural isoflavones, such as genistein, and their semisynthetic derivatives or the pharmaceutically accepted salts thereof may be used for therapeutic and/or prophylactic treatment of diseases, at the base of which lies an excessive production or storage of glycosaminoglycans.

The compounds are administered to the patient as the sole agents or as the components of a combined treatment, combining the compounds with the agents of confirmed therapeutic status in the treatment of mucopolysaccharidoses, for example with the enzymatic replacement therapy.

In one embodiment of the invention, the compounds are represented by formula (I)

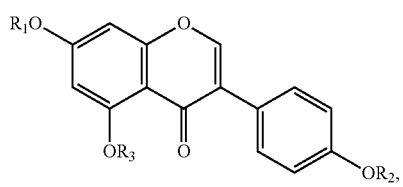

in which:
$R_1$ and $R_2$ are the same or different and are independently H or alkyl, alkenyl, aryl alkylaryl, alkylcarbonyl, arylcarbonyl or mono-, di- or oligosaccharide group, each of them optionally substituted by at least one acyl, alkyl, cycloalkyl, alkoxyalkyl, aryl, alkylaryl, carboxyl or cyano; and
$R_3$ is H, acyl or alkyl.

In certain embodiments of the invention, $R_1$ is H, alkyl, alkenyl, aryl, alkylaryl, alkylcarbonyl, arylcarbonyl, or a monosaccharide group, a disaccharide group, or an oligosaccharide group; $R_2$ is H, alkyl, alkenyl, aryl, alkylaryl, alkylcarbonyl, or arylcarbonyl; and $R_3$ is H or alkyl.

In certain embodiments of the invention, $R_1$ is H, $C_{1-3}$-alkyl, allyl, phenyl, benzyl, $C_{1-3}$-alkylcarbonyl, carbonyl, benzoyl, a monosaccharide group or a disaccharide group, each of these optionally substituted by either $C_{1-15}$-acyl, oxiranyl, $C_{1-4}$-alkoxyl or carboxyl; $R_2$ is H, $C_{1-3}$-alkyl, benzyl, $C_{1-3}$-alkylcarbonyl, carbonyl, each of these optionally substituted by either acetyl, $C_{1-3}$-alkyl, $C_{1-3}$-alkoxyl, or carboxyl; and $R_3$ is H, acetyl, or $C_{1-3}$-alkyl.

In certain embodiments of the invention, the compound of formula (I) is genistein.

In certain embodiments of the invention, the compound of formula (I) is not genistein.

The isoflavones and derivatives thereof may be administered to the patient as such or, preferably, in the form of a pharmaceutical composition, comprising a therapeutically effective amount of at least one isoflavone or its semisynthetic derivative represented by the formula (I) or the pharmaceutically acceptable salt thereof as an active ingredient, together with a pharmaceutically acceptable vehicle and/or excipient.

Under the term "therapeutically effective amount" of isoflavone or its derivative represented by the formula (I) understood will be an amount, which is efficient in treatment and/or prevention of at least one type of mucopolysaccharidose, which means that the amount will be sufficient for limitation of GAG synthesis and/or for reducing the amount of the deposits accumulated in cells and at the same time ensuring low toxicity, tolerated by the patient. In the case of genistein, the beneficial therapeutic effect is observed within concentrations of about 10-20 micromoles/l.

Selection of a therapeutically effective dose of the active ingredient and dosage regimen of isoflavones and their derivatives depends on the type of disorder, age, weight and condition of the patient and they are determined by a specialist on the basis of results of clinical trials and a general knowledge of the condition.

According to the invention, the daily dose of a derivative of isoflavone adjusted to the body mass of the patient, can amount to from 1 to 50 mg/kg of a body mass depending on the way of administration, and particularly about 5 mg/kg of a body mass.

The daily dose of the active ingredient can be administered to the patient in the unit dosage form once per day or several times per day, optionally in a combination with other agents being therapeutically effective in the treatment of mucopolysaccharidoses. Such agents can be administered concurrently in the form of a combined formulation with a fixed dose or in separate formulations administered parallel or subsequently in the order and time intervals determined by a specialist.

The pharmaceutical composition, according to the invention, may be in any accepted in the pharmaceutical practice form, suitable for oral, parenteral, intranasal, sublingual, rectal, inhalatory or any other, administration. Especially the pharmaceutical composition may be in the form of tablet, pill, capsule, powder, granules, sterile solution or suspension, aerosol or suppository.

The proper methods of preparation of particular pharmaceutical forms according to the accepted practice, described for instance in the publication Remington's Pharmaceutical Sciences, Gennaro, ed. Mack Publishing Co., Easton, Pa. 1990, and are known to the skilled in the art.

The solid forms, like tablets, pills, powders, granules or capsules, are prepared by accurate mixing the active ingredient with a pharmaceutical vehicle, such as corn starch, lactose, saccharose, sorbitol, talc, stearic acid, magnesium stearate, dicalcium phosphate or gum as well as other pharmaceutical diluents, for instance water, for formation of the solid premix, comprising the homogeneous mixture of compound according to the invention or to its pharmaceutically acceptable salt. The obtained in such a way premix can be used for tableting, making dragees or for filling capsules. Tablets or granules of the composition can be coated or prepared in other way to obtain a unit dosage form providing beneficially prolonged action. For production of such protecting or coating layers one can use several different substances, comprising different polymeric acids and their mixtures with such additives as shellac, cetyl alcohol or cellulose acetate.

The liquid forms of pharmaceutical compositions suitable for oral administration or for injection, according to the invention, comprise aqueous solutions, syrups, aqueous or oil suspended solids, emulsions with edible oils, such as cotton plant seed oil, sesame oil, coconut or peanut oil, as well as elixirs with similar pharmaceutical vehicles. Appropriate dispersing or suspending agents for aqueous suspended solids comprise synthetic and natural gums such as tragacanth, acacia, alginates, dextran, sodium carboxymethyl cellulose, methyl cellulose, polyvinyl pyrrolidone or gelatine.

The pharmaceutical composition in a solid form for oral administration may be in the form of tablet, capsule or granulate.

The solid oral formulation comprises at least one derivative of isoflavone dispersed within the vehicle together with other pharmaceutically acceptable excipients, such as binders, disintegrants and lubricants.

The proper vehicle (filler) will be selected by those skilled in the art, depending upon the required ready to use form of the medicine. Especially preferred diluent or filler of the solid pharmaceutical forms is lactose in different forms including the anhydrous, hydrated and spray-dried one. The most required form of lactose one can choose by considering the required solubility, homogeneity of substance comprised in the preparation, hardness, embrittlement and decomposition time of the tablet or capsule.

The binder, useful in the granulation stage, will be selected depending on the admissible viscosity and required hydration. Especially preferred binder is hydroxypropyl cellulose, especially the micromolecular one or microcrystalline cellulose.

The disintegrant, which applies to both granulates and loose powders, making easier the process of their decomposition, will be chosen from the group comprising different grades of starch, derivatives of cellulose, pectins, alginic acid and alginates, polivinylopirolidon. The preferred disintegrant is cross-linked polivinylopirolidon.

The proper lubricants, preventing sticking and crushing of tablets in the tabletting machine, are for instance calcium or magnesium stearate, paraffin, cetyl or stearyl alcohol. A preferred lubricant is magnesium stearate.

The solid pharmaceutical forms can be coated with a polymer selected from the group consisting of hydroxypropylmethyl cellulose, hydroxyethyl cellulose, hydroxymethylethyl cellulose, sodium salt of carboxymethyl cellulose, polivinylopirolidon, copolymers of methacrylic and acrylic acids esters, methyl and ethyl cellulose, as coating and subcoating layer, warranting its physical stability.

Appropriate coatings for using on the hydroxypropylmethyl cellulose layer constitute dry mixtures of components, which could be dispersed in water and used as aqueous dispersion for coating solid preparations with a film. For example, the coating consist of hydroxypropylmethyl cellulose, polyethylene glycol, polysorbate 80 and titanium dioxide. If necessary the solid preparation could be polished in a known manner, for instance with carnauba wax.

EXAMPLES

Example 1

Biological Tests

The activity of isoflavones was evaluated by the measure of glycosaminoglycans synthesis in 35S-sulphate incorporation test comprising incubation of the radiolabelled 35S-sulfate into GAGs in cultured human skin fibroblasts derived from normal individuals (control) and patients affected with mucopolysaccharidose (Murata et al., Arch Biochem Biophys 2003; 413: 229-235).

As shown in FIG. 1, the level of glycosaminoglycans synthesis in the presence of genistein is significant decreasing in cultured human skin fibroblasts derived both from normal individuals and those affected with MPS 1.

Figure 2:
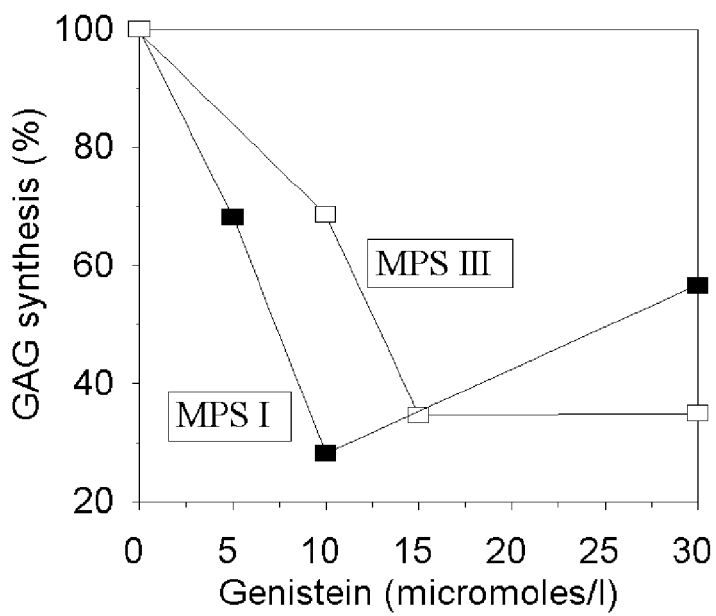
FIG. 2 shows GAG synthesis in fibroblasts derived from individuals with different MPS types in presence of genistein.

As shown in FIG. 2, tests have proved that glycosaminoglycans synthesis will be also significantly reduced in the presence of genistein in cells derived from individuals with other types of MPS.

The activity of inhibiting glycosaminoglycans synthesis demonstrates also a soya extract rich in isoflavones. As the tested compound there was used a commercial available soya extract enriched with isoflavones (Soyfem® from Biofarm, Poznan, Poland). The results of tests indicating the inhibition of GAG synthesis in the presence of Soyfem® in cultured fibroblasts are represented in FIG. 3.

Figure 4:
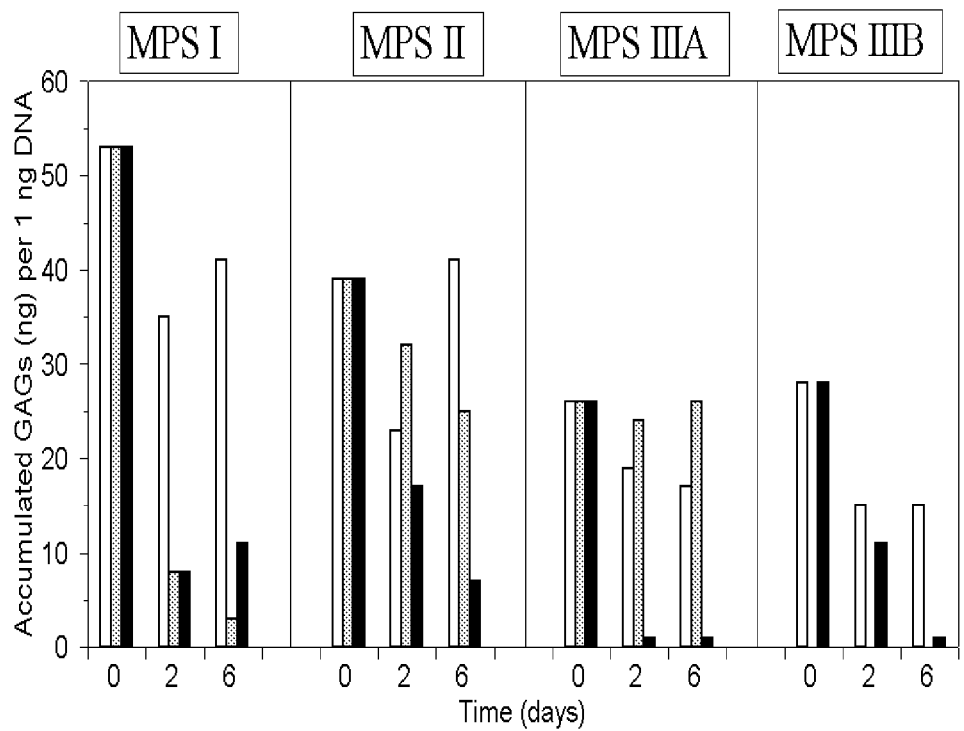
FIG. 4 shows activities of recombinant human α-L-iduronidase (100 U/1000 ml; gray columns), genistein (10 micromoles/l; black columns) against GAG deposits, and empty columns represents control.

As shown in FIG. 4, further tests have proved that in the presence of genistein in the fibroblasts cells derived from patients affected with different MPSs not only takes place the inhibition of glycosaminoglycans accumulation but also their deposits are gradually removed.

Specifically, as shown in FIG. 4, after few days of cultivation under such conditions the effectiveness of removing GAG accumulated in cells derived from human individuals was comparable with the activity of recombinant human α-L-iduronidase (Aldurazyme). The electron microscope observation confirmed the phenomenon of decline of the before accumulated glycosaminoglycans from cells cultured in the presence of genistein and derivatives of isoflavones.

Figure 3:
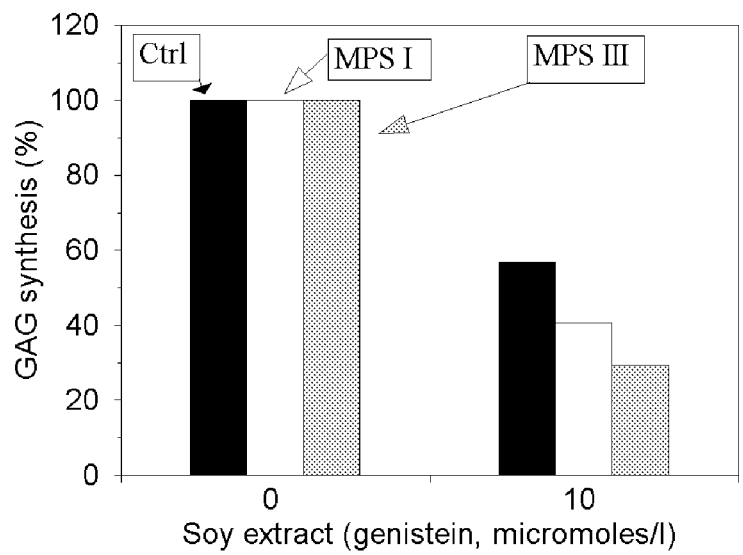
FIG. 3 shows GAG synthesis in fibroblasts in the presence of soya isoflavones extract (Soyfem®)

The activity of genistein and soya isoflavones against the GAG deposits in fibroblasts derived from human individuals affected with different types of MPS is presented in FIG. 3.

The decrease of GAG synthesis and reduction of the deposits accumulated in cells under genistein or soya isoflavones extract action has been observed at genistein concentrations of about 10-20 micromoles/l.

Further screening of semisynthetic derivatives of genistein represented by formula (I) has been performed comparing their activity to genistein as the reference (Table 2). The activity of derivatives of genistein represented by formula (I) in the glycosaminoglycans synthesis has been essayed in the radiolabelled 35S-sulphate incorporation test by using different human cell lines. The negative control was DMSO (diluent for genistein and all derivatives), the positive control—genistein. Genistein and the semisynthetic derivatives thereof were used in concentration of 30 μM. Experiment with each cell line has been repeated twice, and every measurement has been done twice.

TABLE 2

Glycosaminoglycans synthesis in the presence of semisynthetic genistein derivatives

| Compound | Structure | Relative GAG synthesis (converted to 1 cell) | | Inhibition in relation to genistein |
|---|---|---|---|---|
| | | Normal cells | MPS I | |
| Control | | 1 | 1 | –/– |
| Genistein | 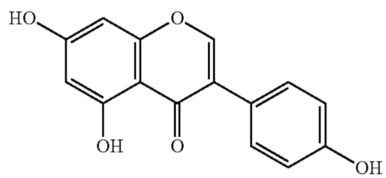 [SMILES: O=c1c(-c2ccc(O)cc2)coc2cc(O)cc(O)c12] | 0.25 | 0.51 | 0 |
| IFG-001 | 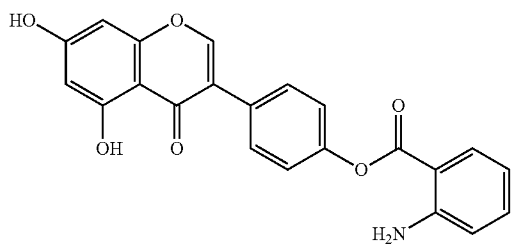 [SMILES: Nc1ccccc1C(=O)Oc1ccc(-c2coc3cc(O)cc(O)c3c2=O)cc1] | 0.84 | 1.70 | –/– |
| IFG-018 | 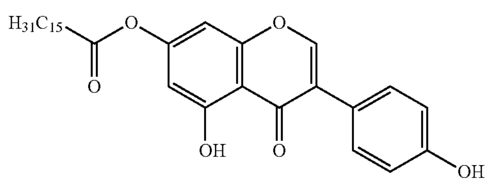 | 0.37 | 0.51 | 0/0 |
| IFG-021 | 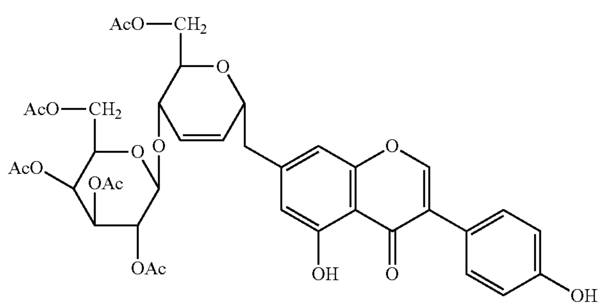 | 0.57 | 0.92 | –/– |
| IFG-027 | 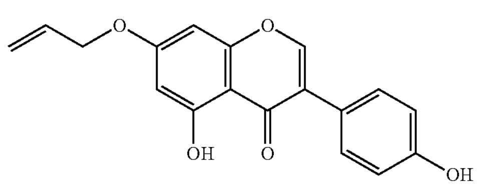 [SMILES: C=CCOc1cc(O)c2c(=O)c(-c3ccc(O)cc3)coc2c1] | 0.22 | 0.57 | 0/0 |
| IFG-032 | 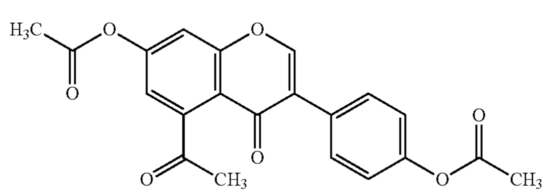 [SMILES: CC(=O)Oc1ccc(-c2coc3cc(OC(C)=O)cc(C(C)=O)c3c2=O)cc1] | 0.25 | 0.68 | 0/– |

TABLE 2-continued

Glycosaminoglycans synthesis in the presence of semisynthetic genistein derivatives

| Compound | Structure | Relative GAG synthesis (converted to 1 cell) | | Inhibition in relation to genistein |
|---|---|---|---|---|
| | | Normal cells | MPS I | |
| IFG-034 | (structure) | 0.40 | 0.93 | −/− |
| IFG-035 | (structure) | 0.26 | 1.17 | 0/− |
| IFG-036 | (structure) | 0.27 | 0.49 | 0/0 |
| IFG-037 | (structure) | 0.29 | 1.66 | 0/− |
| IFG-038 | (structure) | 0.74 | 0.74 | −/− |
| IFG-042 | (structure) | 0.14 | 0.49 | +/0 |
| IFG-043 | (structure) | 0.17 | 0.44 | +/0 |

TABLE 2-continued

Glycosaminoglycans synthesis in the presence of semisynthetic genistein derivatives

| Compound | Structure | Relative GAG synthesis (converted to 1 cell) | | Inhibition in relation to genistein |
|---|---|---|---|---|
| | | Normal cells | MPS I | |
| IFG-046 | TsO(H$_2$C)$_2$O(H$_2$C)$_2$O(H$_2$C)$_2$O-[isoflavone structure with OH groups] | 1.80 | 0.49 | −/0 |
| IFG-048 | [isoflavone structure with HO, OH, and OCH$_2$COOC(CH$_3$)$_3$ groups] | 0.70 | 0.92 | −/− |
| IFG-050 | [isoflavone structure with epoxide-methylene-O and OH groups] | 0.10 | 0.73 | +/− |
| IFG-051 | [isoflavone structure with benzyloxy, OH, and allyloxy groups] | 0.32 | 0.96 | 0/− |
| IFG-052 | [isoflavone structure with allyloxy, OH, and acetylsalicylate ester groups] | 0.75 | 0.85 | −/− |

TABLE 2-continued

Glycosaminoglycans synthesis in the presence of semisynthetic genistein derivatives

| Compound | Structure | Relative GAG synthesis (converted to 1 cell) | | Inhibition in relation to genistein |
|---|---|---|---|---|
| | | Normal cells | MPS I | |
| IFG-053 | | 0.30 | 0.52 | 0/0 |
| IFG-054 | | 0.30 | 0.53 | 0/0 |
| IFG-060 | | 0.43 | 0.31 | −/+ |
| IFG-061 | | 0.28 | 0.46 | 0/0 |
| IFG-062 | | 3.16 | 5.61 | ---/--- |

TABLE 2-continued

Glycosaminoglycans synthesis in the presence of semisynthetic genistein derivatives

| Compound | Structure | Relative GAG synthesis (converted to 1 cell) | | Inhibition in relation to genistein |
|---|---|---|---|---|
| | | Normal cells | MPS I | |
| IFG-063 | 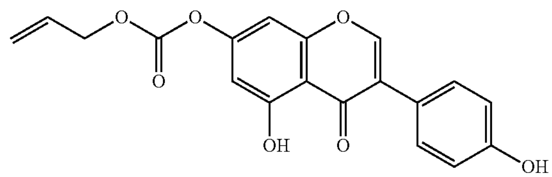 [SMILES: C=CCOC(=O)Oc1cc(O)c2c(=O)c(-c3ccc(O)cc3)coc2c1] | 0.75 | 1.87 | –/– |
| IFG-064 | 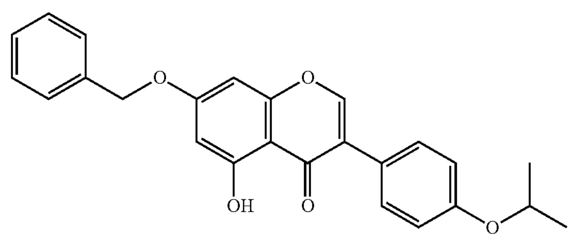 [SMILES: CC(C)Oc1ccc(-c2coc3cc(OCc4ccccc4)cc(O)c3c2=O)cc1] | 0.68 | 0.60 | –/– |
| IFG-065 | 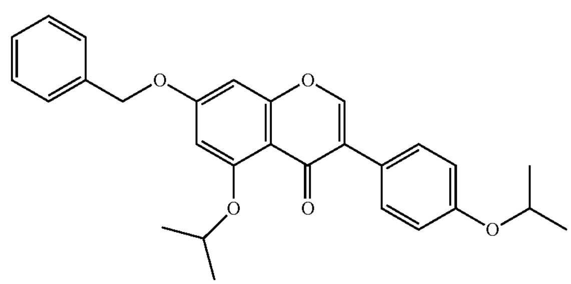 [SMILES: CC(C)Oc1ccc(-c2coc3cc(OCc4ccccc4)cc(OC(C)C)c3c2=O)cc1] | 1.52 | 0.97 | –/– |
| IFG-066 | 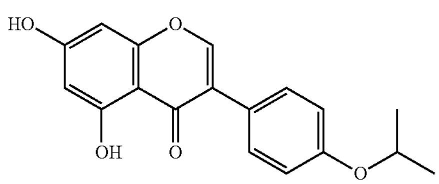 [SMILES: CC(C)Oc1ccc(-c2coc3cc(O)cc(O)c3c2=O)cc1] | 0.23 | 0.44 | 0/0 |
| IFG-067 | 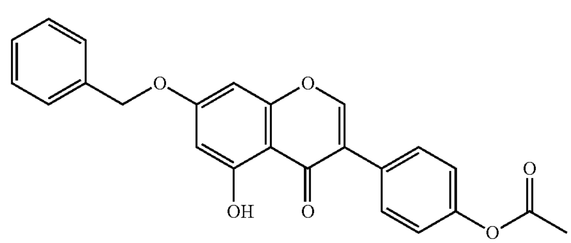 [SMILES: CC(=O)Oc1ccc(-c2coc3cc(OCc4ccccc4)cc(O)c3c2=O)cc1] | 0.67 | 0.61 | –/– |

"–" inhibition weaker than by genistein;
"0" inhibition comparable to genistein;
"+" inhibition stronger than by genistein.

The compounds IFG-18, IFG-42 and IFG-50 have demonstrated in the above test stronger influence on GAG synthesis than genistein, and the compounds IFG-27, IFG-36, IFG-38, IFG-43 and IFG-53—an activity comparable with genistein. The compounds IFG-32, IFG-35, IFG-48, IFG-51, IFG-52 and IFG-64 showed an activity comparable with genistein, but only for one cell line.

The results of the above experiments confirmed the potential usefulness of derivatives of isoflavone presented by formula (I) in the treatment and/or prevention of mucopolysaccharidoses.

Example 2

Tablet Formulation

| | |
|---|---|
| Genistein | 50 mg |
| Corn starch | 16 mg |
| Colloidal silicon dioxide | 1 mg |
| Magnesium stearate | 1 mg |
| K-30 povidone | 3 mg |
| Pregelatinized starch | 4 mg |
| Microcrystalline cellulose | 25 mg |
| Lactose | 200 mg |

Example 3

Capsule Formulation

| | |
|---|---|
| Genistein | 10 mg |
| Corn starch | 2 mg |
| Colloidal silicon dioxide | 0.2 mg |
| Magnesium stearate | 0.4 mg |
| Lactose | 20 mg |

This invention is not to be limited to the specific embodiments disclosed herein and modifications for various applications and other embodiments are intended to be included within the scope of the appended claims. While this invention has been described in connection with particular examples thereof, the true scope of the invention should not be so limited since other modifications will become apparent to the skilled practitioner upon a study of the drawings, specification, and following claims.

All publications and patent applications mentioned in this specification are indicative of the level of skill of those skilled in the art to which this invention pertains. All publications and patent applications mentioned in this specification are herein incorporated by reference to the same extent as if each individual publication or patent application mentioned in this specification was specifically and individually indicated to be incorporated by reference.

What is claimed is:

1. A pharmaceutical composition comprising: a pharmaceutically acceptable excipient; and a compound of formula (I):

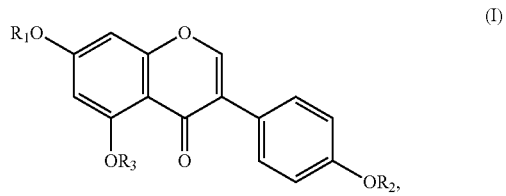

or a pharmaceutically acceptable salt thereof,
wherein:
$R_1$ is H, allyl, or $R_1$ is $C_{1-3}$-alkyl, benzyl, benzoyl, $C_{1-3}$-alkylcarbonyl, each of these optionally substituted by oxiranyl, $C_{1-4}$-alkoxyl or carboxyl;
$R_2$ is H, $C_{1-3}$-alkylcarbonyl, or $R_2$ is $C_{1-3}$-alkyl, benzyl, each of these optionally substituted by $C_{1-3}$-alkyl, $C_{1-3}$-alkoxyl or carboxyl; and
$R_3$ is H, or $C_{1-3}$-alkyl; and
wherein the compound of formula (I) is not genistein.

2. The composition of claim 1, wherein:
$R_1$ is allyl, or $R_1$ is $C_{1-3}$-alkyl, benzyl, benzoyl, $C_{1-3}$-alkylcarbonyl, each of these optionally substituted by oxiranyl, $C_{1-4}$-alkoxyl or carboxyl;
$R_2$ is H, $C_{1-3}$-alkylcarbonyl, or $R_2$ is $C_{1-3}$-alkyl, benzyl, each of these optionally substituted by $C_{1-3}$-alkyl, $C_{1-3}$-alkoxyl or carboxyl; and
$R_3$ is H, or $C_{1-3}$-alkyl.

3. The composition of claim 1, wherein:
$R_1$ is H, allyl, or $R_1$ is $C_{1-3}$-alkyl, benzyl, benzoyl, $C_{1-3}$-alkylcarbonyl, each of these optionally substituted by oxiranyl, $C_{1-4}$-alkoxyl or carboxyl;
$R_2$ is $C_{1-3}$-alkylcarbonyl, or $R_2$ is $C_{1-3}$-alkyl, benzyl, each of these optionally substituted by $C_{1-3}$-alkyl, $C_{1-3}$-alkoxyl or carboxyl; and
$R_3$ is H, or $C_{1-3}$-alkyl.

4. The composition of claim 1, wherein:
$R_1$ is H, allyl, or benzyl;
$R_2$ is H, $C_{1-3}$-alkyl, or $C_{1-3}$-alkylcarbonyl; and
$R_3$ is H, or $C_{1-3}$-alkyl.

5. The composition of claim 4, wherein:
$R_1$ is allyl, or benzyl;
$R_2$ is H, $C_{1-3}$-alkyl, or $C_{1-3}$-alkylcarbonyl; and
$R_3$ is H, or $C_{1-3}$-alkyl.

6. The composition of claim 4, wherein:
$R_1$ is H, allyl, or benzyl;
$R_2$ is $C_{1-3}$-alkyl, or $C_{1-3}$-alkylcarbonyl; and
$R_3$ is H, or $C_{1-3}$-alkyl.

7. The composition of claim 5, wherein $R_3$ is H.

8. The composition of claim 6, wherein $R_3$ is H.

9. A pharmaceutical composition comprising: a pharmaceutically acceptable excipient; and a compound selected from the group consisting of 4'-(2-aminobenzoyloxy)-5,7-dihydroxy-3-phenylchromen-4-one; 4',5-dihydroxy-7-hexadecanoyloxy-3-phenylchromen-4-one; 2-(acetoxymethyl)-6-(2-(acetoxymethyl)-6-((5-hydroxy-3-(4-hydroxyphenyl)-4-oxo-4H-chromen-7-yl)methyl)-3,6-dihydro-2H-pyran-3-yloxy)tetrahydro-2H-pyran-3,4,5-triyl triacetate; 4',5-dihydroxy-7-allyloxy-3-phenylchromen-4-one; 4',5-dihydroxy-7-(2-hydroxybenzoyloxy)-3-phenylchromen-4-one; 4',7-diallyloxy-5-hydroxy-3-phenylchromen-4-one; 4',5-dihydroxy-7-propionyloxymethoxy-3-phenylchromen- 4-one; 4',5-dihydroxy-7-(tert-butoxycarbonylmethoxy)-3-phenylchromen-4-one; 4',5-dihydroxy-7-(4-carboxybutyryloxy)-3-phenylchromen-4-one; 4',7-di(tert-butoxycarbonylmethoxy)-5-hydroxy-3-phenylchromen-4-one; 4',5-dihydroxy-7-benzyloxy-3-phenylchromen-4-one; 2-(2-(2-(5-hydroxy-3-(4-hydroxyphenyl)-4-oxo-4H-chromen-7-yloxy)ethoxy)ethoxy)ethyl 4-methylbenzenesulfonate; 4'-(tert-butoxycarbonylmethoxy)-5,7-dihydroxy-3-phenylchromen-4-one; 4',5-dihydroxy-7-oxiranylmethoxy-3-phenylchromen-4-one; 3-(4-(allyloxy)phenyl)-7-(benzyloxy)-5-hydroxy-4H-chromen-4-one; 4-(7-(allyloxy)-5-hydroxy-4-oxo-4H-chromen-3-yl)phenyl 2-acetoxybenzoate; 4'-(3,5-bis(1-cyano-1-methylethyl)benzyloxy)-5-hydroxy-7-benzyloxy-3-phenylchromen-4-one; 4',5-dihydroxy-7-carboxymethoxy-3-phenylchromen-4-one; 2-(5-hydroxy-3-(4-hydroxyphenyl)-4-oxo-4H-chromen-7-yloxy)acetic acid; 4'-(4-carboxybutyryloxy)-5-hydroxy-7-benzyloxy-3-phenylchromen-4-one; 4',5-dihydroxy-7-(4-methoxybenzyloxy)-3-phenylchromen-4-one; allyl 5-hydroxy-3-(4-hydroxyphenyl)-4-oxo-4H-chromen-7-yl carbonate; 7-(benzyloxy)-5-hydroxy-3-(4-isopropoxyphenyl)-4H-chromen-4-one; 7-(benzyloxy)-5-isopropoxy-3-(4-isopropoxyphenyl)-4H-chromen-4-one; 5,7-dihydroxy-3-(4-isopropoxyphenyl)chromen-4-one; 4'-acetoxy-5-hydroxy-7-benzyloxy-3-phenylchromen-4-one; and a pharmaceutically acceptable salt thereof.

10. A method for the treatment of mucopolysaccharidosis, the method comprising administering to a patient in the need thereof a therapeutically effective amount of the compound of formula (I):

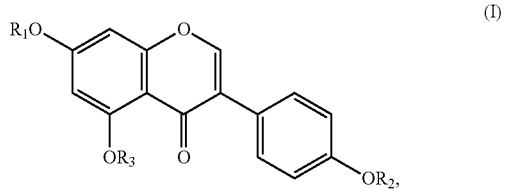

or a pharmaceutically acceptable salt thereof, wherein:
$R_1$ is H, allyl, or $R_1$ is $C_{1-3}$-alkyl, benzyl, benzoyl, $C_{1-3}$-alkylcarbonyl, each of these optionally substituted by oxiranyl, $C_{1-4}$-alkoxyl or carboxyl;
$R_2$ is H, $C_{1-3}$-alkylcarbonyl, or $R_2$ is $C_{1-3}$-alkyl, benzyl, each of these optionally substituted by $C_{1-3}$-alkyl, $C_{1-3}$-alkoxyl or carboxyl; and
$R_3$ is H, or $C_{1-3}$-alkyl; and
wherein the compound of formula (I) is not genistein.

11. The method of claim 10, wherein:
$R_1$ is allyl, or $R_1$ is $C_{1-3}$-alkyl, benzyl, benzoyl, $C_{1-3}$-alkylcarbonyl, each of these optionally substituted by oxiranyl, $C_{1-4}$-alkoxyl or carboxyl;
$R_2$ is H, $C_{1-3}$-alkylcarbonyl, or $R_2$ is $C_{1-3}$-alkyl, benzyl, each of these optionally substituted by $C_{1-3}$-alkyl, $C_{1-3}$-alkoxyl or carboxyl; and
$R_3$ is H, or $C_{1-3}$-alkyl.

12. The method of claim 10, wherein:
$R_1$ is H, allyl, or $R_1$ is $C_{1-3}$-alkyl, benzyl, benzoyl, $C_{1-3}$-alkylcarbonyl, each of these optionally substituted by oxiranyl, $C_{1-4}$-alkoxyl or carboxyl;
$R_2$ is $C_{1-3}$-alkylcarbonyl, or $R_2$ is $C_{1-3}$-alkyl, benzyl, each of these optionally substituted by $C_{1-3}$-alkyl, $C_{1-3}$-alkoxyl or carboxyl; and
$R_3$ is H, or $C_{1-3}$-alkyl.

13. The method of claim 10, wherein:
$R_1$ is H, allyl, or benzyl;
$R_2$ is H, $C_{1-3}$-alkyl, or $C_{1-3}$-alkylcarbonyl; and
$R_3$ is H, or $C_{1-3}$-alkyl.

14. The method of claim 13, wherein:
$R_1$ is allyl, or benzyl;
$R_2$ is H, $C_{1-3}$-alkyl, or $C_{1-3}$-alkylcarbonyl; and
$R_3$ is H, or $C_{1-3}$-alkyl.

15. The method of claim 13, wherein:
$R_1$ is H, allyl, or benzyl;
$R_2$ is $C_{1-3}$-alkyl, or $C_{1-3}$-alkylcarbonyl; and
$R_3$ is H, or $C_{1-3}$-alkyl.

* * * * *